United States Patent [19]

Kurland

[11] Patent Number: 4,653,482

[45] Date of Patent: Mar. 31, 1987

[54] UPPER-EXTREMITY TRACTION TRAY ATTACHMENT FOR OPERATING TABLES

[76] Inventor: Kenneth Z. Kurland, 2 W. McCabe Rd., El Centro, Calif. 92243

[21] Appl. No.: 735,159

[22] Filed: May 17, 1985

[51] Int. Cl.$^{4}$ .................................... A61F 5/04

[52] U.S. Cl. .................................... 128/71; 5/443; 5/507; 128/84 R; 269/328

[58] Field of Search .................... 5/507, 508, 431, 443; 128/75, 84 R, 69, 71; 269/328

[56] References Cited

U.S. PATENT DOCUMENTS

| | | | |
|---|---|---|---|
| 420,143 | 1/1890 | Colbert | 5/507 |
| 883,325 | 3/1908 | MacMillan | 128/84 R |
| 1,980,848 | 11/1934 | Cass | 269/328 |
| 2,796,061 | 6/1957 | Miller | 128/75 |
| 3,423,773 | 1/1969 | Yamate | 5/443 |
| 3,814,414 | 6/1974 | Chapa | 269/328 |
| 3,844,550 | 10/1974 | McGuire | 269/328 |
| 3,875,356 | 4/1975 | Heim | 5/431 |

FOREIGN PATENT DOCUMENTS

| | | | |
|---|---|---|---|
| 740848 | 11/1932 | France | 5/507 |

OTHER PUBLICATIONS

Wolfmann, Photo of Cylinders Adjustable in Slotted Support.

*Primary Examiner*—Clyde I. Coughenour
*Attorney, Agent, or Firm*—Charmasson & Holz

[57] ABSTRACT

A tray for attachment to the edge of an operating table which provides horizontal support form the arm, wrist and hand, or leg of a patient during surgical operations on those parts of the body. The tray comprises a perimetric rectangular metal frame having a pair of spaced-apart, downward-facing, L-shaped projections on each side. Any side of the frame may be secured to the side rail of a typical operating table by securing any of the projection pairs to the side rail on either side of a typical operating table with the common screw-type clamps which may be anchored at any point along the rail. A rigid rectangular sheet of material transparent to both X-rays and visible light spans the gap between the two longitudinal frame sections, a gap being left at either end between the lateral edges of the sheet and each lateral frame section. Traction pulley mounting arm and adjustable support leg assemblies or adjustable support leg assemblies may be mounted on either or both lateral frame sections, which are of circular cross-section. The sheet of transparent material has a lateral slot near one end. An elbow post may be slideably mounted at its base within the slot.

6 Claims, 9 Drawing Figures

FIG. 2
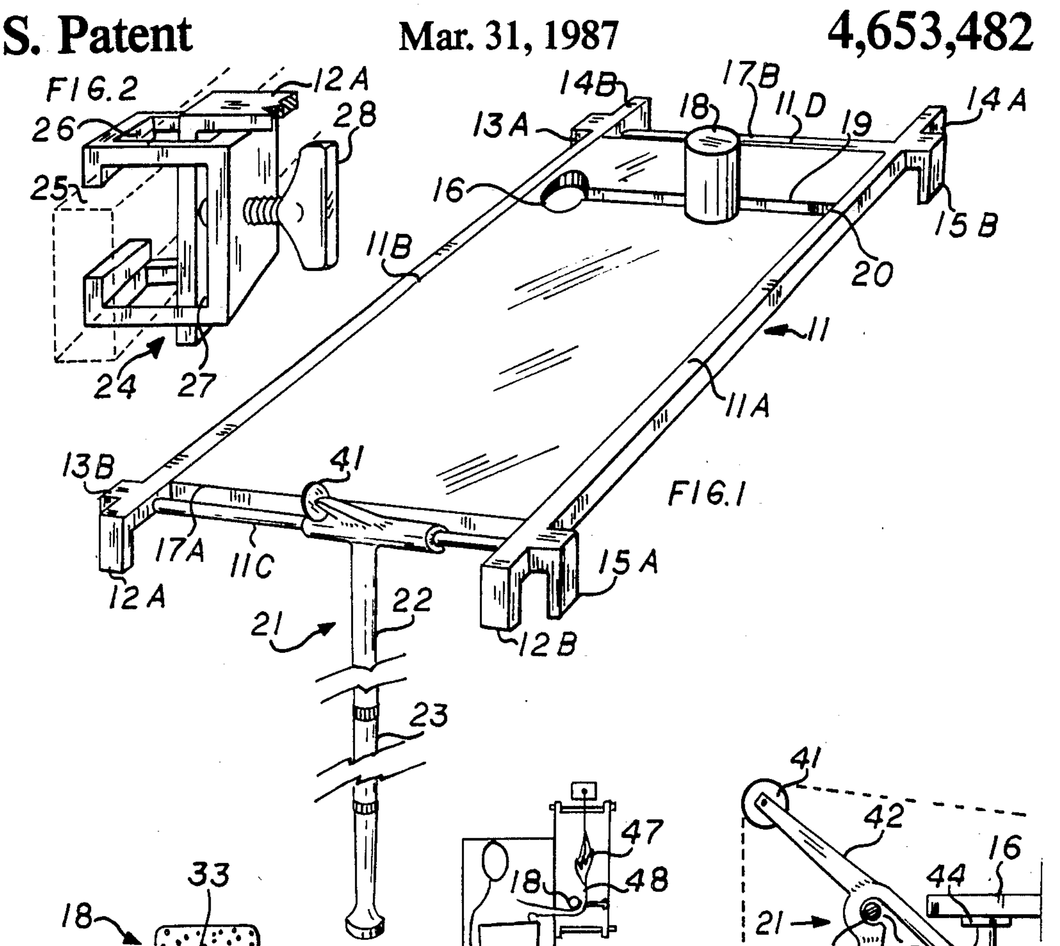
FIG. 1
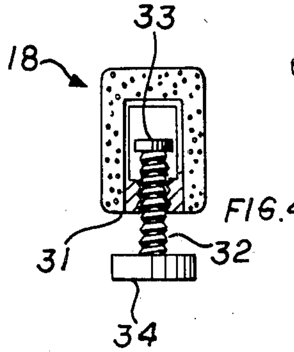
FIG. 4
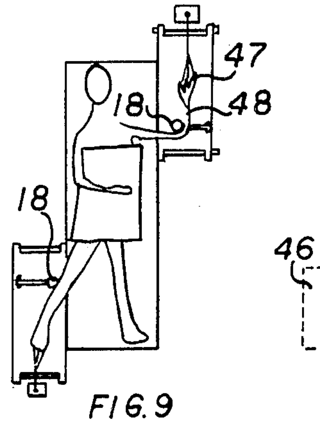
FIG. 9
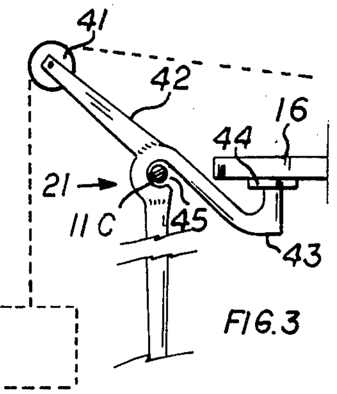
FIG. 3
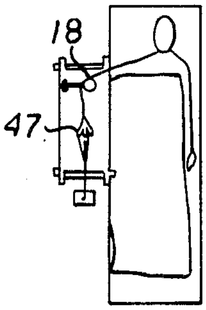
FIG. 8
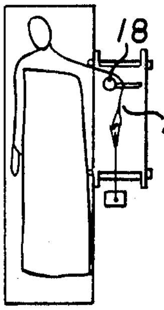
FIG. 7
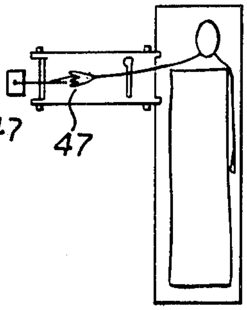
FIG. 5
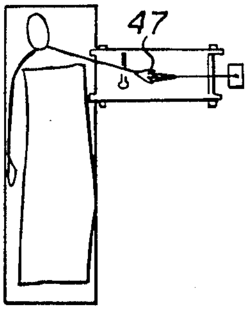
FIG. 6

UPPER-EXTREMITY TRACTION TRAY ATTACHMENT FOR OPERATING TABLES

FIELD OF THE INVENTION

The present invention relates to operating tables, operating table attachments, and traction devices.

BACKGROUND OF THE INVENTION

Contemporary operating tables are designed primarily to facilitate the performance of surgical operations on the head, torso and legs. Heretofore, wrist, hand and forearm surgery has often been performed with the arm suspended in the air; the four fingers of a hand are inserted in diagonally-woven tubular devices much like the Chinese finger traps which constrict, grasping the finger, when stretched. Such a suspension method does not provide optimum stability for performing delicate operations, nor does it facilitate the taking of X-ray photographs. It would be very desireable to support the arm of the patient on a firm, horizontal, radiolucent surface in a state of traction. Such a position would facillitate both the taking of X-ray photographs and the performance of complex forearm, wrist and hand surgery.

SUMMARY OF THE INVENTION

The primary objective of the present invention is to provide a rectangular traction tray which may be attached in a horizontal position to the side edges of a standard operating table. The tray comprises a perimetric rectangular metal frame having a pair of spaced-apart, downward-facing, L-shaped projections on each side. Any edge of the frame may be secured to the side rail on either side of a standard operating table by securing any of the projection pairs to the side rail with the common screw-type clamps which may be anchored at any point along the rail. A rigid rectangular sheet of material transparent to both X-rays and visible light spans the gap between the two longitudinal frame sections, a gap being left at either end between the lateral edges of the sheet and each lateral frame section. Traction pulley mounting arms and adjustable legs may be mounted on either or both lateral frame sections, which are of circular cross-section. A padded cylindrical elbow post is slideably mounted at its base in a lateral slot near one end of the sheet of transparent material.

When the tray is attached to the operating table by one of its longitudinal edges, the end of the tray having the elbow post is normally mounted closed to the head of the table. The patient's arm may be bent at the elbow, with the elbow post positioned at the inside of the bend. The patient's forearm then rests approximately parallel to his body, and the hand may be comfortably placed in a down-turned position. The elbow post has sufficient lateral travel so that the tray may be used for either arm by attaching the right longitudinal edge of the tray to the left rail of the operating table or the left longitudinal edge of the tray to the right rail of the operating table. In order to stabilize the arm, a traction and tray-support assembly is mountable at the lower end of the tray. The Chinese finger-trap technique may be employed to connect the tips of the fingers to a weight draped over a pulley mounted on the traction assembly and tray-support assembly. Alternatively, skeletal traction may be employed in conjunction with the tray.

The upper lateral edge of the tray may be attached to either longitudinal edge of of the operating table. In this position, the patient's arm may be outstretched so that it is essentially perpendicular to his body, with the hand in an up-turned position. In this case, the elbow post is removed, as it is not needed. As before, the traction assembly and Chinese finger-trap technique may be used as a stabilizing measure.

BRIEF DESCRIPTION OF THE DRAWINGS

FIG. 1 is a perspective view of the tray, with the elbow post and traction assembly attached;

FIG. 2 is a perspective view of a side-rail clamp;

FIG. 3 a partial side elevational view of the detachable traction assembly;

FIG. 4 is a cross-sectional view of the elbow post; traction assembly;

FIG. 5 illustrates the use of the traction tray for performing surgery to the outstretched right arm (palm raised);

FIG. 6 the use of the traction tray for performing surgery to the outstretched left arm (palm raised);

FIG. 7 illustrates the use of the traction tray for performing surgery to the bent left arm (palm down);

FIG. 8 illustrates the use of the traction tray for performing surgery to the bent right arm (palm down); and FIG. 9 illustrates the use of the traction tray for performing foot and lower-leg surgery, as well as an alternate way to perform left arm palm-raised surgery.

DESCRIPTION OF THE PREFERRED EMBODIMENT OF THE INVENTION

Referring now to FIG. 1, the traction tray comprises a perimetric rectangular metal frame 11 having a pair of spaced-apart, downward-facing, L-shaped projections (12A, 12B; 13A, 13B; 14A, 14B; and 15A, 15B) on each outer edge thereof. A rigid rectangular sheet of material transparent to both X-rays and visible light 16 spans the gap between longitudinal frame sections 11A and 11B, with a gap being left at each end of the tray between the lateral edges 17A and 17B of sheet 16 and lateral frame sections 11C and 11D, respectively. Padded cylindrical elbow post 18 may be removably and slideably mounted at its base in lateral slot 19, which is located near one end of transparent sheet 16. Circular hole 20 is cut at the end of slot 19. Traction assembly 21, which is shown mounted on lateral frame section 11C, incorporates support leg 22. The height of support leg 22 may be adjusted with an oppositely-threaded screw arrangement by rotating leg center section 23.

Referring now to FIG. 2, clamp 24 is typical of the screw-type clamps which may be mounted at any point on the side rail 25 of a typical operating table. Any pair of L-shaped projections (12A, 12B; 13A, 13B; 14A, 14B; or 15A, 15B) may be anchored to the side rail 25 of an operating table by inserting the vertical portion of each of said pair of L-shaped projections through upper opening 26 and lower opening 27 of a clamp 24, and then securing each of said pair of L-shaped projections to rail 25 by means of wing-head screw 28.

Referring now to FIG. 4, elbow post 18 comprises a hollow cylindrical member 31 into which anchoring screw 32 is threadably installed. Because peened end 33 prevents removal of anchoring screw 32 from cylindrical member 31, elbow post 18 is installed in slot 19 by inserting head 34 of screw 32 through circular hole 20 at the end of slot 19. Elbow post 18 can then be anchored at any point within slot 19.

FIG. 3 shows the detail of traction assembly 21. Traction cord pulley 41 is rotatably mounted at the end of pulley arm 42. Rotational stop arm 43 prevents traction assembly 21 from rotating about the lateral frame member 11C, which is of circular cross section. Stop arm pad 44 is shown resting against transparent sheet 16. Traction assembly 21 may be removably installed on either of the lateral frame members 11C or 11D by slipping the lateral frame member into groove 45. A traction weight 46 is shown in broken lines, suspended from a cord draped over pulley 41.

The support assembly 21 may be implemented without the pulley arm and pulley. Such assembly could be attached to either lateral frame member when only a supporting function is desired.

For surgical procedures involving the palm of either hand, the tray is attached to an operating table as shown in FIGS. 5 and 6. Elbow post 18 is removed from the tray, and traction assembly 21 is attached at the end of the tray opposite the attachment end. In order to stabilize the arm, Chinese finger traps 47 may be attached to the fingers of the subject hand, with cords attached thereto being draped over the pulley of traction assembly 21 and anchored to a weight of optimum weight.

For surgical procedures involving the back of the hand, the tray is attached to an operating table to that lateral slot 19 is nearest the head of the operating table, as shown in FIGS. 7 and 8. The patient's arm is then bent at the elbow, with elbow post 18 positioned at the inside of the bend. The patient's forearm then rests approximately parallel to his body, and the hand may be comfortably placed in a down-turned position. Elbow post 18 has sufficient lateral travel within slot 19 so that the tray may be used for supporting either arm in the bent position. In order to stabilize the arm when in the bent position, traction assembly 21 may be mounted at the lower end of the tray so that the Chinese finger-trap technique may be employed.

FIG. 9 illustrates the use of the tray in performing ankle or foot surgery as well as an alternate manner of performing palm-raised hand surgery using the elbow rest 18 in order to stabilize the upward bent forearm 48. The traction-tray is thus a versatile attachment to a standard operating table or gurney. The applications described above are only illustrative and are not intended to limit its utility.

While the preferred embodiment of the invention has been described and modifications thereto have been suggested, other applications may be devised without departing from the spirit of the invention and the scope of the appended claims.

What is claimed is:

1. For use in combination with an operating table of the type having longitudinal rails on either side and mounting clamps having upper and lower openings for receiving equipment-anchoring projections slideably mounted thereon, a tray clampable to either of said rails for operating on the limb of a patient lying on said table comprising:

a perimetric rectangular metal frame having a pair of spaced-apart, downward-facing, L-shaped projections on each of its four edges;

said L-shaped projections being sized and shaped to fittingly engage the openings of said mounting clamps; and an essentially rectangular sheet of rigid material scanning the distance between the longitudinal sections of said frame and having a transversal slot spaced apart and parallel to the shorter edges of said frame;

an elbow post slideably mounted within said slot; and means attached to one of said shorter edges for applying traction to said limb in a direction perpendicular to said slot.

2. The tray of claim 1 wherein at least one lateral frame member is of circular cross-section and spaced from the nearest parallel edge of said rectangular sheet.

3. The tray of claim 2 which further comprises a support leg which is removably attachable to said at least one lateral frame member.

4. For use in combination with an operating table of the type having longitudinal rails on either side and mounting clamps having upper and lower openings for receiving equipment-anchoring projections slideably mounted thereupon, a traction tray clampable to either of said rails comprising:

a perimetric rectangular metal frame having a pair of spaced-apart, downward-facing, L-shaped projections on at least one edge;

said L-shaped projections being sized and shaped to fittingly engage the upper and lower openings of said mounting clamps;

an essentially rectangular sheet of rigid transparent material spanning the distance between the longitudinal sections of said frame and having a lateral slot cut therein;

an elbow post slidably mounted within said slot;

wherein at least one lateral frame member is of circular cross-section and spaced from the nearest parallel edge of said rectangular sheet;

a support leg assembly removably attachable to said at least one lateral frame member and having a projecting pulley arm to which is rotatably attached a traction cord pulley.

5. The tray of claim 4 wherein said support leg assembly has a projecting rotational stop arm, the end of which rests against the bottom of said rectangular sheet.

6. The tray of claim 5 wherein said rectangular sheet is transparent to both visible light and X-rays.

* * * * *